United States Patent [19]

George et al.

[11] Patent Number: 5,382,725
[45] Date of Patent: Jan. 17, 1995

[54] PROCESS FOR THE PURIFICATION OF 1,3-DIHALOBENZENE FROM AN ISOMERIC MIXTURE OF DIHALOBENZENES

[75] Inventors: Jacob George, Newark; Kantilal B. Desai, New Castle; Francis M. Schoeffler, Port Penn, all of Del.

[73] Assignee: Standard Chlorine of Delaware Inc., Delaware City, Del.

[21] Appl. No.: 198,901

[22] Filed: Feb. 18, 1994

[51] Int. Cl.$^6$ .................. C07C 22/00; C07C 17/38
[52] U.S. Cl. ........................ 570/211; 570/177; 570/178
[58] Field of Search .............. 570/211, 177, 178

[56] References Cited

U.S. PATENT DOCUMENTS

| | | | |
|---|---|---|---|
| 2,798,891 | 7/1957 | Schaeffer et al. | 260/674 |
| 2,958,708 | 11/1960 | Fleck et al. | 260/650 |
| 3,170,961 | 2/1965 | Britton et al. | 260/650 |
| 4,996,380 | 2/1991 | McCulloch et al. | 570/211 |

FOREIGN PATENT DOCUMENTS

| | | |
|---|---|---|
| 0044366 | 1/1982 | European Pat. Off. . |
| 0105524 | 4/1984 | European Pat. Off. . |
| 0253661 | 1/1988 | European Pat. Off. . |
| 0278680 | 8/1988 | European Pat. Off. . |
| 0451720 | 10/1991 | European Pat. Off. . |
| 2855940 | 12/1979 | Germany . |
| 3229677 | 10/1983 | Germany . |
| 3617137 | 11/1986 | Germany . |
| 3538565 | 5/1987 | Germany . |
| 4011501 | 10/1991 | Germany . |
| 49-17247 | 4/1974 | Japan . |
| 52-62229 | 5/1977 | Japan . |
| 53-44528 | 4/1978 | Japan . |
| 53-105434 | 9/1978 | Japan . |
| 54-160322 | 12/1979 | Japan . |
| 57-31627 | 2/1982 | Japan . |
| 58-174336 | 10/1983 | Japan . |
| 1-313446 | 12/1989 | Japan . |
| 2-164835 | 6/1990 | Japan . |
| 3-188031 | 8/1991 | Japan . |
| 78610 | 8/1975 | Poland . |
| 1460061 | 2/1989 | U.S.S.R. . |

Primary Examiner—Alan Siegel
Attorney, Agent, or Firm—Darby & Darby

[57] ABSTRACT

1,3-dihalobenzene, particularly 1,3-dichlorobenzene, is produced in high efficiency from a mixture containing the subject compound and its corresponding 1,4-isomer by a special process in which the dihalobenzene mixture is treated with polyethylene glycols of varying molecular weight and the resulting slurry is filtered to remove a complex of 1,4-dihalobenzene and polyethylene glycol as a solid and the 1,3-dihalobenzene as the filtrate.

The 1,4-dihalobenzene complexed with the polyethylene glycol can be recovered by a flash distillation under vacuum and the residue containing the polyethylene glycol can be recycled.

The purity of the 1,3-dihalobenzene obtained by this process can further be improved by subjecting the product obtained after the polyethylene glycol treatment to a low temperature crystallization process where 1,3-dihalobenzene can be selectively crystallized to a purity of above 99%.

26 Claims, No Drawings

PROCESS FOR THE PURIFICATION OF 1,3-DIHALOBENZENE FROM AN ISOMERIC MIXTURE OF DIHALOBENZENES

BACKGROUND OF THE INVENTION

This invention relates to a process for the purification of 1,3-dihalobenzenes, particularly 1,3-dichlorobenzene, and their separation from a mixture of corresponding 1,4- and 1,3-dihalobenzenes. The purification of 1,3-dihalobenzene is accomplished by selectively removing the 1,4-isomer as a complex with polyethylene glycol. The process according to the invention produces 1,3-dihalobenzenes in high purity.

1,3-dichlorobenzene is a commercially important intermediate compound which serves as a building block in the synthesis of many products that are important to both the pharmaceutical and agricultural industries. The direct synthetic routes to produce 1,3-dichlorobenzene are limited and are economically unfeasible. Normally, 1,3-dichlorobenzene is co-produced along with other dichlorobenzenes by the chlorination of benzene. Similarly, dichlorobenzenes can be isomerized to a mixture containing predominantly 1,3-dichlorobenzene.

The recovery of 1,3-dichlorobenzene from mixtures of other dichlorobenzenes, particularly 1,4-dichlorobenzene, is one of the most difficult separations in aromatic chemistry. Normally, the separation and/or purification of these organic chemicals is carried out by distillation or crystallization. In the case of 1,3- and 1,4-dichlorobenzene, separation via the distillation route is practically impossible due to their narrow difference in the boiling points (less than 0.2° C. apart from one another). Similarly, the purification of 1,3-dichlorobenzene from a mixture of 1,4- and 1,3-dichlorobenzenes by crystallization is also impossible due to the formation of an eutectic mixture where both compounds freeze at the same temperature. The eutectic point for 1,4- and 1,3-dichlorobenzene mixture is approximately −29.4° C. and consists of approximately 88% 1,3-dichlorobenzene and 12% 1,4-dichlorobenzene. Up to or closer to the eutectic point, 1,4-dichlorobenzene can be removed from the mixture in high purity by crystallization. However, in the proximity of the eutectic point, removal of 1,4-dichlorobenzene by crystallization becomes difficult and therefore the purity of 1,3-dichlorobenzene can not be improved further. At eutectic point and lower temperatures, both 1,4- and 1,3-dichlorobenzene freezes together. If the composition changes such that the mixture contains more than 88% 1,3-dichlorobenzene, the crystallization at or above −29.4° C. will yield pure 1,3-dichlorobenzene. But to achieve the concentration of 1,3-dichlorobenzene required for its purification through crystallization is very difficult.

Because of the difficulty in the separation and purification of 1,3-dichlorobenzene, several complicated and expensive options have been suggested and commercially practiced to produce high purity 1,3-dichlorobenzene. For example, the reaction of metachloronitrobenzene with $SOCl_2$ (Beilstein V-243, V1-(129), metabenzenesulfonic acid with $SOCl_2$ (Beilstein XI-68, XI1-(21), and metabromonitrobenzene with $PCl_5$ (Beilstein V-248, V1-(131) have been described.

U.S. Pat. No. 3,170,961 describes a process of extracting 1,3-dichlorobenzene from a mixture of 1,4- and 1,3-dichlorobenzenes by a bromination route. In this process, during the bromination step, the 1,3-isomer is selectively reacted to form 1-bromo-2,4-dichlorobenzene which is separated from the 1,4-dichlorobenzene by distillation. The bromodichlorobenzene is debrominated in a second step in the presence of a bromine acceptor, e.g. benzene, and aluminum chloride as the catalyst. This process is complicated and expensive and produces undesirable by-products such as hydrogenbromide gas and bromobenzene.

Other purification processes, such as the one described in U.S. Pat. No. 2,958,708, include the physical separation of the 1,3-isomer with various agents, such as a molecular sieve. While this process provides the desired purity of 1,3-dichlorobenzene, the regeneration of the molecular sieve is very difficult. This process is also not cost effective.

Japanese patent JP 89,313,446 (application JP 01,313,446) describes a process to purify 1,3-dichlorobenzene by forming an inclusion complex between this isomer and a host compound, such as 9,9'-bianthracene, and distillation of the complex from 1,4-dichlorobenzene at a temperature lower than the decomposition point of the complex. This process has several shortcomings, such as requiring the handling of toxic compounds and lack of cost effectiveness.

U.S. Pat. No. 4,996,380 describes another process for separating 1,3-dichlorobenzene from a mixture of dichlorobenzenes using the selective absorption characteristics of certain zeolites. While high purity 1,3-dichlorobenzene can be produced by the use of this technique, this process becomes expensive since the zeolites can not be used indefinitely. Also, an additional solvent (which needs to be removed subsequently through distillation) is required to extract the absorbed 1,3-dichlorobenzene.

Another method to separate 1,3-dichlorobenzene from a mixture of 1,4- and 1,3-dichlorobenzenes is described in German patent 2,855,940. It uses combination of distillation and crystallization. In this process the crude dichlorobenzene mixture is distilled to first increase the concentration of the 1,3-dichlorobenzene to approximately 90%. The distillate is then subjected to a crystallization to extract the pure 1,3-dichlorobenzene. After the separation of the 1,3-dichlorobenzene, the mother liquor is recycled to the distillation stream to further increase its purity to 90%. Even though this method produces high purity 1,3-dichlorobenzene, it requires a distillation column with a large number of stages. Therefore, this process becomes very difficult to practice and economically unattractive.

Belgium patent BE 897,296 describes a process for the concentration of 1,4-dichlorobenzene using a thin film (100-u) of very high molecular weight ($5 \times 10^6$) glycols to increases its concentration to 70%. However, high purity 1,3-dichlorobenzene is not produced. Moreover, such high molecular weight thin film glycols are not commercially available.

German patent 23 32 889 and European patent application 0 451 720 describe methods to separate 1,3-dichlorobenzene from a mixture containing 1,3- and 1,4-dichlorobenzenes. Both processes use an extractive rectification technique using different extractants. For instance, the German patent uses hexamethyl phosphoric acid triamide and the European patent uses alkylene carbonates. Various other compounds, such as dimethyl sulfoxide, n-ethyl pyrolidone and dibutyl sulfoxide, have been described as possible extractants for this process. However, some of these substances are toxic, corrosive, unstable, and their boiling points unfavorable for high temperature distillation.

In view of the deficiencies of the aforementioned prior art processes, it is highly desirable to provide a new process for the purification and commercial production of high purity 1,3-dihalobenzenes from a mixture containing its corresponding 1,4-disubstituted isomer.

SUMMARY OF THE INVENTION

The present invention relates to a process for separating 1,3-dihalobenzene from a mixture of 1,4-dihalobenzene and 1,3-dihalobenzene, comprising treating the mixture with a polyethylene glycol to form a complex of polyethylene glycol and 1,4-dihalobenzene. The complex is separated from the reaction mixture by vacuum filtration. This process is repeated until the concentration of 1,3-isomer in the filtrate reaches a predetermined amount. The filtrate is then distilled to recover the 1,3-dihalobenzene and remove any residual polyethylene glycol.

The process of the present invention can be performed on any dihalobenzene with the preferred dihalobenzenes for treatment being dichlorobenzene and dibromobenzene.

The purity of the 1,3-dihalobenzene obtained by the treatment of polyethylene glycol ranges from 95 to 97%. This is sufficiently pure for the normal commercial use. For special applications, where higher purity is required, the product can be further purified to up to 99.95% by a selective solidification using a static crystallizer.

The polyethylene glycol used in the process may be recovered and reused. Normally, the polyethylene glycol is recovered by distillation.

The process of the present invention can also be used to purify 1,3-dihalobenzene from a mixture of 1,2-dihalobenzene, 1,3-dihalobenzene and 1,4-dihalobenzene.

Additionally, the present invention is directed to a composition consisting of the complex of polyethylene glycol and 1,4-dihalobenzene.

DETAILED DESCRIPTION OF THE INVENTION

In the process of the present invention, 1,3-dihalobenzene is selectively isolated from an isomeric mixture containing 1,3- and 1,4-dihalobenzenes by the use of polyethylene glycol.

The polyethylene glycol can be in the form of fine particles (as powder), pellets, or granules. While the ultimate absorption of the 1,4-dihalobenzene during the process is not affected by the form (especially in processes involving dihalochlorobenzene), the powder needed less reaction time. preferred molecular weight of the polyethylene glycol is 5,000 to 10,000 although PEG with a molecular weight of 500-50,000 can be used. The molecular weight of the PEG normally is not independently determined. The supplier certifies the molecular weight and grade of PEG when purchased. The grade of polyethylene glycol has little effect in the overall process.

For an effective removal of the 1,4-dihalobenzenes from mixture of 1,3- and 1,4-dihalobenzene, a sufficient amount of the polyethylene glycol must be added to the mixture. The required purity determines the amount of polyethylene glycol used. For example, to raise the purity of 1,3-dichlorobenzene from 80% to 90% in a mixture of 1,4- and 1,3-dichlorobenzenes or bring the dichlorobenzene mixture away from the eutectic point for further processing elsewhere, a minimum amount of polyethylene glycol is used. Normally, the polyethylene glycol required for this purpose varies from 20 to 60% in weight, preferably 30 to 40%, in relation to the amount of 1,4-dichlorobenzene present in the mixture. To achieve higher purity for the 1,3-dichlorobenzene, the amount of the polyethylene glycol used should be equal in weight to that of the 1,4-dichlorobenzene in the mixture. This is the amount normally used in the process.

The complexing step is carried out in batch operation. Immediately upon the addition of the polyethylene glycol to the mixture of dihalobenzenes, the temperature is raised to about 45° C. For optimum complex formation, the temperature range is 15° to 65° C., preferably 35° to 45° C. The dihalobenzene mixture is kept at the optimum temperature for about 30 minutes under agitation. The time required for the complex formation at the optimum temperature is from about 15 minutes to 1 hour, preferably from about 25 to 35 minutes.

At the end of complex formation, the material is cooled to room temperature. For an efficient and complete complex formation of polyethylene glycol with the 1,4-dihalobenzene, the cooling cycle may require sub-ambient temperatures. A normal temperature range for the cooling cycle for 1,4- and 1,3-dichlorobenzene mixture is $-15°$ to 25° C., preferably about 12° to 18° C., and more preferably about 15° C. Depending on the dihalobenzenes, the optimum temperature ranges may vary during the complexing and cooling cycles.

During the complex formation cycles, the reaction mixture requires continuous agitation. The agitation speed must be controlled such that an optimum complex formation can be achieved. Controlled agitation is also particularly important during the cooling cycles when the complex material starts to precipitate. Excessive agitation increases the fine particles which are formed and thereby results in the inefficient removal of the 1,4-isomer.

The requirement for the final purity of the 1,3-dihalobenzene is critical in determining how the purification steps need to be carried out. If the expected purity is below 92%, a one step process can be implemented. If the purity requirement exceeds 92%, multiple treatments of polyethylene glycol are useful. Carrying out the reaction in different steps and cooling the reaction mixture to $-5°$ C. prior to filtration provides higher purity 1,3-dichlorobenzene as compared to the one step reaction. However, attempts to increase the purity of the 1,3-dihalobenzenes above 96% using this process considerably reduces its efficiency due to poor yield.

After formation of the complex, it must be separated from the 1,3-dihalobenzene by filtration under vacuum. The preferred mode of filtration employs 10 $\mu M$ or 25 $\mu M$ filter paper and a vacuum at about 150 mm of Hg.

The filtrate is then distilled to recover the 1,3-dihalobenzene in the overhead and to remove any residual polyethylene glycol.

If it is desired to produce 98 to 99.9% pure 1,3-dihalobenzene, a combination of the polyethylene glycol process axed a final purification step using a static crystallizer should be considered. In such cases, the polyethylene glycol treatment should be limited to increasing the purity of the 1,3-dihalobenzene above the eutectic point and then subjecting the material to a crystallization process.

A static crystallizer is preferred for the crystallization of the 1,3-dihalobenzene due to its crystal characteristics and for better yield. To improve the purity and yield of the process, a two or three stage crystallization is preferred. The crystallization preferably takes place in 20m³ vats. The first stage requires very low temperature to initiate the crystallization. For the crystallization of 1,3-dichlorobenzene from a mixture of 1,4- and 1,3-dichlorobenzenes, a temperature of −33° to −38° C. is preferred during the first stage of the process. The feed material containing the dichlorobenzene isomers is kept at −33° to −35° C. for a period of 1 to 9 hours depending on the size of the crystallizer. At the end of the crystallization cycle, the material is subjected to a melt cycle preferably to about −15° C. for 1,3-dichlorobenzene) and the product and the reject are separated. Normally the melt cycle is carried out very slowly. Preferably the time required to reach the desired temperature is 1 to 12 hours. The first cycle crystallization can be carried out in one crystallizer or in multiple crystallizers, in parallel.

The 1,3-dihalobenzene from the first cycle normally has a purity of 97 to 98%. This can be further improved to 99% by using a second stage crystallization. The second stage crystallization is normally carried out at slightly higher temperature, preferably very close to the melting/freezing point of the 1,3-dihalobenzene. For 1,3-dichlorobenzene isomer, a temperature of −28° C. is ideal for the second stage crystallization. If the reject material from the crystallizer is below the eutectic point, it is then subjected to another polyethylene glycol treatment to improve the 1,3-isomer content before being fed to the crystallizer.

The polyethylene glycol used during the complex formation can be recovered and reused. Typically the spent polyethylene glycol is distilled under very high vacuum, preferably less than 10 mm of Hg, to recover the absorbed organic matter from the polyethylene glycol. Once the organic matter is removed, the polyethylene glycol is suitable for another round of selective absorption. It is not essential that the recovered polyethylene glycol from the distillation be collected as an overhead product. It also can be transferred from the still bottom directly to another selective reaction system.

In the case of dichlorobenzene, if the mixture contains any 1,2-dichlorobenzene, it will not be significantly affected by the polyethylene glycol treatment and will be collected in the filtrate. This may be removed by distillation to achieve high purity for 1,3-dichlorobenzene.

The following examples are illustrative of the present invention, however, it will be understood that the invention is not limited to the specific details set forth therein.

EXAMPLE 1

In this example, a mixture of dichlorobenzenes containing 1,4-, 1,3- and 1,2-dichlorobenzene isomers is used to illustrate the ability of polyethylene glycol to remove 1,4-dichlorobenzene (p-DCB) selectively from a mixture containing both 1,2- and 1,3-dichlorobenzenes. This also illustrates the effect of polyethylene glycol loading in the removal of p-DCB. In this example, a 50% loading of polyethylene glycol with a molecular weight of 8,000 is used.

The reaction was carried out in a round bottom flask. Dichlorobenzene (250 grams) with a composition of 53.61% 1,3-dichlorobenzene, 21.70% 1,4-dichlorobenzene and 24.18% 1,2-dichlorobenzene was charged into the reaction flask. Powdered polyethylene glycol (27.12 grams) with a molecular weight of 8,000 was added to the reaction flask. The material was slowly heated to 50° C. while stirring for a period of 20 to 25 minutes. When all the polyethylene glycol dissolved in the reaction mass, the heating and the stirring was discontinued and the material was slowly cooled down to room temperature (18° to 20° C). The cooled reaction mass was filtered through a 10 μM filter paper using a vacuum at about 150 mm of Hg.

The results obtained in Example 1 are summarized in Table 1.

EXAMPLES 2–4

Examples 2–4 were carried out as described in Example 1, using the same starting material and reaction conditions, except increasingly higher loading of polyethylene glycol was used in each subsequent example. The amount and percentage of polyethylene glycol loading, as well as a summary of results obtained in each example, is set forth in Table 1. These four examples illustrate the effect of increasingly higher loading of polyethylene glycol in the removal of 1,4-dichlorobenzene. As shown in Table 1, the higher the loading of the polyethylene glycol used in the method, the purer the 1,3-dichlorobenzene obtained in the final product.

TABLE 1

EFFECT OF INCREASED PEG LOADING
EXAMPLES 1 THROUGH 4

| | | FEED | | | | | |
|---|---|---|---|---|---|---|---|
| EXAMPLE NUMBER | WEIGHT OF PEG ADDED (Grams) | % PEG LOADING[3] | WEIGHT OF FEED (Grams) | % 1,3 DCB | % 1,4 DCB | % 1,2 DCB | 1,3 DCB SELECTIVITY % |
| 1 | 27.12 | 50 | 250 | 53.61 | 21.7 | 24.18 | 71.19 |
| 2 | 40.69 | 75 | 250 | 53.61 | 21.7 | 24.18 | 71.19 |
| 3 | 54.25 | 100 | 250 | 53.61 | 21.7 | 24.18 | 71.19 |
| 4 | 67.8 | 125 | 250 | 53.61 | 21.7 | 24.18 | 71.19 |

| | | PRODUCT | | | | |
|---|---|---|---|---|---|---|
| EXAMPLE NUMBER | WEIGHT OF PRODUCTS (Grams) | % 1,3 DCB | % 1,4 DCB | % 1,2 DCB | 1,3 DCB SELECTIVITY[1] % | 1,3 DCB YIELD[2] % |
| 1 | 193 | 62.2 | 9.95 | 27.85 | 86.21 | 89.56 |
| 2 | 161 | 66.1 | 6.15 | 27.19 | 91.48 | 79.4 |
| 3 | 122 | 68.5 | 4.9 | 26.6 | 93.32 | 62.35 |

TABLE 1-continued
EFFECT OF INCREASED PEG LOADING
EXAMPLES 1 THROUGH 4

| | 4 | 82 | 68.7 | 4.8 | 26.5 | 93.46 | 42.03 |

NOTE:
[1] 1,3 DCB Selectivity (%) = $\frac{1,3 \text{ DCB} \times 100}{1,3 \text{ DCB and } 1,4 \text{ DCB}}$
either the % or the weight in gm may be used
[2] 1,3 DCB yield (%) = $\frac{\text{Weight in gm 1,3 DCB in the product} \times 100}{\text{Weight in gm 1,3 DCB in the feed}}$
[3] PEG loading is based on the amount of 1,4-dichlorobenzene present in the feed.

EXAMPLE 5

This example illustrates the effect of polyethylene glycol to remove 1,4-dichlorobenzene from a mixture containing only 1,3- and 1,4-dichlorobenzenes. Polyethylene glycol, in a powdered form and having a molecular weight 8,000, was loaded to 100% by weight to that of 1,4-dichlorobenzene. The reaction was carried out as a one step process as described in the previous examples.

Dichlorobenzene (250 grams) with a composition of 75% 1,3-dichlorobenzene and 25% 1,4-dichlorobenzene was charged into a two liter round bottom flask. A powdered form of polyethylene glycol (62.5 grams) having a molecular weight of 8,000 was charged into the reactor. The reaction mixture was heated to approximately 55° C. and stirred with a mechanical stirrer. The heating and stirring was discontinued (after 25 minutes) once the polyethylene glycol was completely dissolved in the dichlorobenzene mixture. The reaction mixture was cooled to room temperature (18° to 20° C.) and filtered using a 10 μM filter paper under vacuum. The collected filtrate (150 grams) consisted of 92% 1,3-dichlorobenzene and 8% 1,4-dichlorobenzene.

1,3-dichlorobenzene in the starting material: 75%
1,3-dichlorobenzene in the product: 92%
Yield of 1,3-dichlorobenzene: 73.6%
Charge of polyethylene glycol: 100% by weight of 1,4-dichlorobenzene

EXAMPLE 6

This example illustrates the ability of polyethylene glycol to remove 1,4-dichlorobenzene from a mixture containing 1,3- and 1,4-dichlorobenzene, as described in Example 5, with the exception that the polyethylene glycol was added in equal amounts, in two different steps. A powdered form of polyethylene glycol having a molecular weight of 8,000 was used for this reaction.

Step 1: Dichlorobenzene (250 grams) with a composition of 75% 1,3-dichlorobenzene and 25% 1,4-dichlorobenzene was charged into a two liter reaction flask. Polyethylene glycol (31.25 grams) having a molecular weight of 8,000 was added to the reactor and the mixture was heated to 50° C. during a 20 minute period under stirring. During the heating cycle, the polyethylene glycol completely dissolved in the dichlorobenzene mixture. The reaction mixture was then cooled down to room temperature (18° to 20° C.) and filtered using a 10 μM filter paper. The collected filtrate (200 grams) consisted of 86% 1,3-dichlorobenzene and 14% of 1,4-dichlorobenzene.

1,3-dichlorobenzene in the starting material: 75%
1,3-dichlorobenzene in the product: 86%
Yield of 1,3-Dichlorobenzene in Step 1: 91.73%
Charge of polyethylene glycol in Step 1: 50% by weight of 1,4-dichlorobenzene Step 2: The filtrate (200 grams) obtained from Step 1 was further treated with polyethylene glycol as described in Step 1. The material was transferred to a two liter round bottom flask and polyethylene glycol (31.25 grams) was added and processed as described in Step 1. The collected filtrate (153 grams) consisted of 93% 1,3-dichlorobenzene and 7% 1,4-dichlorobenzene.

1,3-dichlorobenzene in the starting material: 86%
1,3-dichlorobenzene present in the product: 93%
Yield of 1,3-dichlorobenzene in Step 2: 82.73%
Over-all yield of 1,3-dichlorobenzene: 75.89%

EXAMPLE 7

This example illustrates the improved performance of polyethylene glycol at low temperatures in removing 1,4-dichlorobenzene from a mixture of 1,3- and 1,4-dichlorobenzenes.

Dichlorobenzene (250 grams) with a composition of 75% 1,3-dichlorobenzene and 25% 1,4-dichlorobenzene was charged into a two liter round bottom reaction flask containing powdered polyethylene glycol (62.5 grams) having a molecular weight of 8,000. The reaction flask was heated slowly to dissolve the polyethylene glycol in the dichlorobenzene mixture. This was achieved at about 50° C. after a 20 minute period, under mechanical stirring. The molten material is then allowed to cool down to around −5° C. in a refrigerated bath. The resultant slush was filtered under vacuum using a 25 μM filter paper. The collected filtrate (46.5 grams) had a composition of 95% 1,3-dichlorobenzene and 5% 1,4-dichlorobenzene.

1,3-dichlorobenzene in the starting material: 75%
1,3-dichlorobenzene in the product: 95%
Yield of 1,3-dichlorobenzene: 23.56%
Polyethylene glycol loading: 100% by weight to that of 1,4-dichlorobenzene
Filtration temperature: −4° to 2° C.

EXAMPLE 8

This example illustrates that a higher yield is achieved by carrying out the polyethylene glycol treatment in two steps, instead of one step. This example was carried out as described in Example 7, except two steps were used.

Step 1: Dichlorobenzene (250 grams) containing 75% 1,3-dichlorobenzene and 25% 1,4-dichlorobenzene was charged into a two liter reaction flask containing of powdered polyethylene glycol (31.25 grams) having a molecular weight of 8,000. The reaction flask was heated slowly for about 20 minutes (to about 50° C.) under mechanical stirring to dissolve the polyethylene glycol in the dichlorobenzene mixture. At the end of the heating cycle, the stirring was discontinued and the material was slowly cooled down to around −5° C. in a refrigerated bath. The resultant slurry was filtered under vacuum using a 25 μM filter paper. The filtrate (130 grams) consisting of 88% 1,3-dichlorobenzene and 12% 1,4-dichlorobenzene was collected as the product.

1,3-dichlorobenzene in the starting material: 75%
1,3-dichlorobenzene in the product: 88%
Yield of 1,3-dichlorobenzene in Step 1: 61%
Polyethylene glycol loading in Step 1: ½ of 100% by weight to that of 1,4-dichlorobenzene
Filtration temperature in Step 1: −4° to 2° C.

Step 2: The filtrate (130 grams) collected from Step 1 was further treated with polyethylene glycol using the procedure as described in Step 1. A fresh loading of polyethylene glycol (31.25 grams) was used during this step. The collected filtrate (72 grams) consisted of 96.5% 1,3-dichlorobenzene and 3.5% 1,4-dichlorobenzene.

1,3-dichlorobenzene in the starting material: 88%
1,3-dichlorobenzene in the product: 96.5%
Yield of 1,3-dichlorobenzene in Step 2: 60.73%
Polyethylene glycol loading in Step 2: ½ of 100% by weight to that of starting 1,4-DCB
Filtration temperature in Step 2: −4° to 2° C.
Overall yield for 1,3-dichlorobenzene: 37.06%

EXAMPLE 9

This example illustrates the efficacy of carrying out the reaction with polyethylene glycol at lower temperature and the ability to recover the organic matter from the spent glycol.

Step 1: Use of polyethylene glycol at lower temperature

Dichlorobenzene (100 grams) with a composition of 51.0% 1,3-dichlorobenzene, 25.9% 1,4-dichlorobenzene and 22.9% 1,2-dichlorobenzene was charged in to a one liter round bottom flask containing powdered polyethylene glycol (26 grams) having a molecular weight of 8,000. The reaction mass was kept at around 25° C. under mechanical agitation for 2 hours. The reaction mass was then filtered at room temperature under vacuum using a 10 μM filter paper. The filtrate (51 grams) with a composition of 63.6% 1,3-dichlorobenzene, 6.59% 1,4-dichlorobenzene and 29.18% 1,2-dichlorobenzene was collected as the product. The wet residue (65.8 grams) was also collected from this step.

1,3-dichlorobenzene in the starting material: 51% (51 grams)
1,3-dichlorobenzene in the product: 63.6% (32.44 grams)
1,4-dichlorobenzene in the starting material: 25.9% (25.9 grams)
1,4-dichlorobenzene in the product: 6.59% (3.36 grams)
Selectivity of 1,3-DCB in the product on the basis of 1,4- and 1,3-DCB's only: 90.6%
Selectivity of 1,3-DCB in the starting material on the basis of 1,4-and 1,3-DCB: 66.31%

Step 2: Recovery of organic matter from the spent polyethylene glycol

The residue (65.8 grams) obtained from Step 1 was transferred in to a 250 ml round bottom three neck flask connected with a vacuum distillation head, condenser, a 200 ml collection flask and a thermometer. The distillation flask was heated to around 85° C. under a vacuum of 5 mm of Hg. The absorbed dichlorobenzene from the polyethylene glycol was distilled off (vapor temperature 65° C.) and collected in the collection flask. The collection was continued until an increase in the distillation temperature was noticed. Heating was then discontinued and samples were collected from the still bottom and the product for analysis of chlorobenzene content. The details of the analysis are given below:

| | I Starting material step 1 | | II Product step 1 | | III Distillate step 2 | | IV Residue step 2 | |
|---|---|---|---|---|---|---|---|---|
| | % | gms | % | gms | % | gms | % | gms |
| 1,3-DCB | 51.00 | 51.00 | 63.60 | 32.40 | 35.82 | 12.31 | 36.36 | 3.80 |
| 1,4-DCB | 25.90 | 25.90 | 6.59 | 3.36 | 49.89 | 17.14 | 29.18 | 3.05 |
| 1,2-DCB | 22.40 | 22.40 | 29.18 | 11.42 | 14.29 | 4.91 | 34.45 | 3.60 |
| Total (grams) | | 100.00 | | 47.18 | | 34.36 | | 10.45 |

Total starting material (Column I): 100 grams
Total recovered materials (Columns I, II, III and IV): 91.99
% Recovery of organics: 91.99%
Total polyethylene glycol recovered: 20.9 grams
% Recovery of polyethylene glycol: 80%

EXAMPLE 10

This example illustrates the efficacy of reusing the recovered polyethylene glycol in the selective absorption of 1,4-dichlorobenzene from a mixture of 1,3- and 1,4 dichlorobenzenes.

Dichlorobenzene (80 grams) with a composition of 75% 1,3-dichlorobenzene and 25% 1,4-dichlorobenzene was charged into a one liter round bottom flask containing the recovered polyethylene glycol from Step 2 of Example 9 (equal to 20.9 grams polyethylene glycol). The reaction mass was slowly heated to around 50° C. during a period of 25 to 30 minutes under mechanical stirring and the polyethylene glycol was dissolved in the organic mass. The reaction mass was then cooled down to room temperature 18° to 20° C.) and the precipitated polyethylene glycol was filtered under vacuum using a 10 μM filter paper. Dichlorobenzene (52 grams) was recovered having a composition of 92% 1,3-dichlorobenzene and 8% 1,4-dichlorobenzene.

1,3-dichlorobenzene in the starting material: 75% (60 grams)
1,4-dichlorobenzene in the starting material: 25% (20 grams)
Polyethylene glycol used: effective 20.9 grams as recycled
1,3-dichlorobenzene in the product: 92% (47.8 grams)

EXAMPLE 11

This example illustrates the efficacy of combining the polyethylene glycol process and a low temperature crystallization process to improve the purity of 1,3-dichlorobenzene to above 98%.

Step 1: Treatment with polyethylene glycol

Dichlorobenzene (250 grams) with a composition of 75% 1,3-dichlorobenzene and 25% 1,4-dichlorobenzene was charged into a two liter reaction flask containing powdered polyethylene glycol (62.5 grams) having a molecular weight of 8,000. The reaction mixture was heated to 50° C. under mechanical stirring to dissolve the polyethylene glycol in the dichlorobenzene mixture. The heating and stirring was discontinued after 30 minutes, when all at the polyethylene glycol dissolved in the dichlorobenzene mixture. The reaction mixture was cooled to around 18° to 20° C. and the precipitate polyethylene glycol was filtered under vacuum using a 10 μM filter paper. The collected filtrate (145 grams) consisted of 92% 1,3-dichlorobenzene and 8% 1,4-dichlorobenzene.

% of 1,3-dichlorobenzene in the starting material: 75% (187.5 grams )

% of 1,3-dichlorobenzene in the product after treatment with polyethylene glycol: 92% (133.4 grams)
Yield of 1,3-dichlorobenzene in Step 1: 71.1%

Step 2: Low temperature crystallization

The dichlorobenzene obtained from Step 1 was transferred to a laboratory microcrystallization apparatus capable of cooling the charge below −35° C. The crystallizer charge was kept between −30° to −38° C. for around 3 hours. At the completion of the freezing cycle, the temperature of the frozen material was slowly raised to −25° C. and the mother liquor obtained during the process was withdrawn from the crystallizer unit. The frozen material was melted uniformly by increasing the temperature of the crystallizer to around −15° C. The steps involved in the crystallization were repeated for a total of three times. The product (13 grams) collected in the final step had a purity of 99.1% 1,3-dichlorobenzene.

EXAMPLE 12

This example illustrates the efficacy of using polyethylene glycol in the selective removal of 1,4-dibromobenzene from a mixture of 1,4- and 1,3-dibromobenzenes.

A synthetic mixture (30 grams) of 1,3- and 1,4-dibromobenzene with a composition of 67% and 33% respectively was charged into a 250 ml reaction flask containing powdered polyethylene glycol (4 grams) having a molecular weight of 8,000. The reaction mixture was heated to around 60° C. and the polyethylene glycol was dissolved in the dibromobenzene mixture. The material was slowly cooled down to around 20° to 25° C. and filtered through a 10 μM filter paper under vacuum. The product (12.5 grams) having a composition of 86% 1,3-dibromobenzene and 14% 1,4-dibromobenzene was collected as the product.

1,3-dibromobenzene in the starting material: 67% (20.1 grams)
1,4-dibromobenzene in the starting material: 33% (9.9 grams)
1,3-dibromobenzene in the product: 86% (10.75 grams)
1,4-dibromobenzene in the product: 14% (1.75 grams)
Amount of polyethylene glycol used: 40% by weight to that of 1,4-dibromobenzene (4 grams).

EXAMPLE 13

This example shows the use of a polyethylene glycol with a higher molecular weight to remove 1,4-dichlorobenzene from a mixture containing 1,3- and 1,4-dichlorobenzene.

Dichlorobenzene (100 grams) with a composition of 55.31% 1,3-dichlorobenzene, 21.71% 1,4-dichlorobenzene and 22.30% 1,2-dichlorobenzene was charged into a two liter round bottom flask. Granulated polyethylene glycol (22 grams) having a molecular weight of 35,000 was added into the reactor. This constitutes a weight ratio of the polyethylene glycol to 1,4 DCB of 1:1. The reaction mixture was heated to about 80° C. under mechanical stirring. The heating was discontinued (after 25 to 30 minutes) when all of the polyethylene glycol was dissolved in the chlorobenzene mixture. The reaction mixture was then cooled to 18° C. and filtered through a 10 μM filter paper under vacuum. The collected filtrate (48.5 grams) consisted of 69.26% 1,3-dichlorobenzene, 4.27% 1,4-dichlorobenzene and 26.5% 1,2-dichlorobenzene.

Selectivity of 1,3-DCB in starting material (excluding 1,2-DCB): 71.80%
Selectivity of 1,3-DCB in the product (excluding 1,2-DCB): 94.19%
Yield of 1,3-DCB: 60.73%

EXAMPLE 14

Characteristics of Polyethylene glycol DCB complex

The polyethylene glycol complex with dichlorobenzene (mainly 1,4-dichlorobenzene) is a gelantious solid as it separates out in the chlorobenzene mixture. When the complex is filtered and separated from the dichlorobenzene which is not part of the complex, a material is recovered which is a grayish white powder at room temperature. The properties of the complex vary, depending on the molecular weight and the loading of polyethylene glycol in the dichlorobenzene mixture. The following properties were observed for complexes formed by the reacting equal weights of polyethylene glycol having molecular weights of 4,000 and 35,000, respectively, with 1,4-dichlorobenzene.

|  | PEG Complex | PEG Complex |
| --- | --- | --- |
| PEG Molecular weight | 4,000 | 35,000 |
| Color | Off White (cream) | Off White (cream) |
| Appearance | Powder | Powder |
| Melting point; °C. | 72–77 | 75–80 |
| Bulk density; gm/cc | 1.0385 | 1.105 |
| DCB content; (wt/wt) % | ~45 | ~45 |

What is claimed is:

1. A method for separating 1,3-dihalobenzene from a mixture of 1,4-dihalobenzene and 1,3-dihalobenzene, comprising the steps of:
   a) adding to said mixture polyethylene glycol so as to form a complex of said polyethylene glycol with said 1.4-dihalobenzene; and
   b) separating said complex from said treated mixture.
2. The method of claim 1, wherein said dihalobenzene is dichlorobenzene.
3. The method of claim 1, wherein said dihalobenzene is dibromobenzene.
4. The method of claim 1, wherein said polyethylene glycol has a molecular weight in the range of 500–50,000.
5. The method of claim 1, wherein the amount of polyethylene glycol used is about equal, in weight, to the amount of said 1,4-dihalobenzene in said mixture.
6. The method of claim 1, wherein the amount of polyethylene glycol used is about 20–60%, by weight, of the amount of said 1,4-dihalobenzene in said mixture.
7. The method of claim 6, wherein the amount of polyethylene glycol used is about 30–40%, by weight, of the amount of 1,4-dihalobenzene in said mixture.
8. The method of claim 1, wherein all of the polyethylene glycol is added to said mixture at the beginning of step(a).
9. The method of claim 1, wherein the polyethylene glycol is added incrementally during step (a).
10. The method of claim 4, wherein said polyethylene glycol added in step (a) is in a powder form.
11. The method of claim 1, wherein step (a) is performed at a temperature of from about 15° to 65° C., with agitation.
12. The method of claim 11, wherein said temperature is from about 35° to 45° C.

13. The method of claim 12, wherein said complex is formed between about 15 minutes and one hour.

14. The method of claim 13, wherein said complex is formed between about 25 and 35 minutes.

15. The method of claim 11, wherein said complex is further cooled to room temperature prior to step (b).

16. The method of claim 11, wherein said complex is further cooled to a temperature of from about −15° to 25° C. prior to step (b).

17. The method of claim 16, wherein said complex is further cooled to a temperature of from about 12° to 18° C. prior to step (b).

18. The method of claim 17, wherein said complex is further cooled to a temperature of about 15° C.

19. The method of claim 1, further comprising the step of distilling said treated mixture to recover said 1,3-dihalobenzene and to remove residual polyethylene glycol from said 1,3-dihalobenzene after step (b).

20. The method of claim 19, wherein said the 1,3-dihalobenzene is further purified by crystallization.

21. The method of claim 20, wherein said crystallization is static crystallization.

22. The method of claim 21, wherein said crystallization is performed in multiple stages.

23. The method of claim 1, wherein said polyethylene glycol is recovered from said complex by distillation.

24. The method of claim 23, wherein said distillation is performed under a vacuum of less than 10 mm Hg.

25. A method for separating 1,3-dihalobenzene from a mixture of 1,2-dihalobenzene, 1,3-dihalobenzene and 1,4-dihalobenzene, comprising the steps of:
 a) adding to said mixture polyethylene glycol so as to form a complex of said polyethylene glycol with said 1,4-dihalobenzene; and
 b) separating said complex from treated mixture.

26. The method of claim 25, wherein said dihalobenzene is dichlorobenzene.

* * * * *